(12) United States Patent
Sugaya et al.

(10) Patent No.: US 8,105,832 B1
(45) Date of Patent: Jan. 31, 2012

(54) METHODS FOR MODIFYING STEM CELL CHARACTERISTICS

(75) Inventors: Kimonobu Sugaya, Winter Park, FL (US); Angel Alvarez, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 755 days.

(21) Appl. No.: 12/176,647

(22) Filed: Jul. 21, 2008

Related U.S. Application Data

(60) Provisional application No. 60/950,672, filed on Jul. 19, 2007.

(51) Int. Cl.
*C12N 5/07* (2010.01)
*C12N 5/0775* (2010.01)
*C12N 5/02* (2010.01)

(52) U.S. Cl. ......... 435/377; 435/373; 435/372; 435/347

(58) Field of Classification Search .................. 435/377, 435/373, 372, 347
See application file for complete search history.

(56) References Cited

OTHER PUBLICATIONS

Straube et al. (2006), Artificial Organs, vol. 30(10), 743-755.*
Kim et al. (2008) Dev. Dyn., vol. 237(10), 2830-2843.*

* cited by examiner

*Primary Examiner* — Anne Marie S Wehbe
(74) *Attorney, Agent, or Firm* — Timothy H. Van Dyke; Beusse, Wolter, Sanks, Mora & Maire, P.A.

(57) ABSTRACT

The invention provides a method of up-regulating genes in cultured human bone marrow mesenchymal stem cells, the method comprising culturing the stem cells in a nutrient medium together with cells from a limb of a limb-regenerating animal. In the method, the limb-regenerating animal is preferably a species of the family Polychrotidae. Another method of the invention provides for up-regulating genes maintaining pluripotency and proliferation in cultured human bone marrow mesenchymal stem cells by culturing the stem cells in a nutrient medium together with mouse embryonic stem cells.

4 Claims, 2 Drawing Sheets

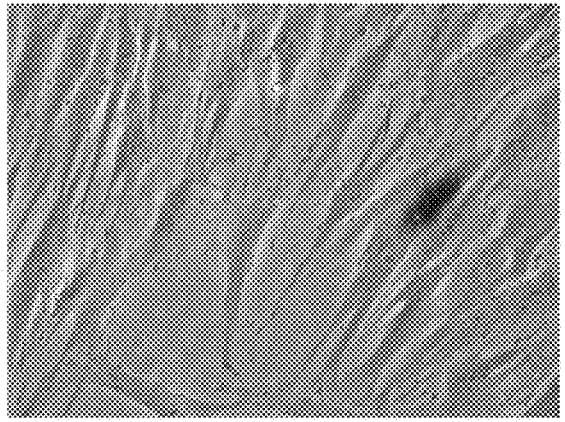
FIG. 1A
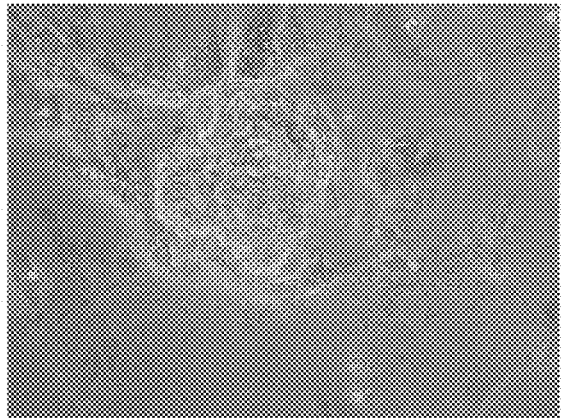
FIG. 1B
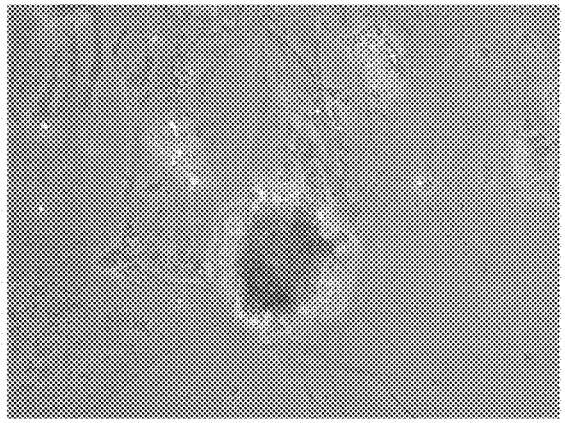
FIG. 1C
FIG. 1

METHODS FOR MODIFYING STEM CELL CHARACTERISTICS

RELATED APPLICATION

This application claims priority from provisional application Ser. No. 60/950,672 which was filed on 19 Jul. 2007 and which is incorporated herein by reference in its entirety.

FIELD OF THE INVENTION

This invention relates to cellular differentiation and, more specifically, to methods of modifying the developmental potential of a cell and, particularly, of stem cells.

BACKGROUND OF THE INVENTION

Every multicellular organism contains stem cells that have the ability to differentiate into any other cell in the body. Because stem cells are essentially precursors of many other cell types, there has been much research interest in elucidating their cellular mechanisms. Imagine the promise of being able to culture replacement tissues or even whole organs from stem cells. Additionally, the potential for using stem cells to repair damaged tissues may be applicable to a wide range of disease conditions.

Mammalian stem cells typically originate from three sources. Embryonic stem cells are obtained from early embryos, particularly the blastocyst stage of embryonic development. Adult stem cells are those which are found in adult tissues, which generally contain at least a small complement of these primordial cells that can further develop into the specialized cells of the particular tissue and thereby provide a repair function. Lastly, cord blood stem cells are obtained from umbilical cord blood obtained around the time of birth.

Embryonic stem cells, in particular, are at the center of a politico-religious controversy focused on the need for destroying a fertile human embryo when harvesting the stem cells. This debate has caused the federal government, at least to date, to deny research funding for projects involving embryonic stem cells.

A stem cell is characterized by the ability to renew itself, that is, it maintains its undifferentiated state while undergoing many cycles of cell division; it proliferates, yet it remains a progenitor cell. Secondly, to be considered a stem cell, it must retain the ability to morph into any other cell type. The term "stem cell" is sometimes also applied to progenitor cells that have the ability to form only a specific type of mature cell.

Stem cells are described by the scope of their potency, that is, by the range of mature cells which the stem cell can differentiate into. Totipotent stem cells possess the broadest developmental ability and can form any other downstream cells. Totipotent stem cells are formed very early in the embryonic cycle, for example, from a fertilized egg and its first few divisions. Pluripotent stem cells develop from totipotent cells and have the ability to form cells of any of the three germ layers in the body: ectoderm, endoderm and mesoderm.

In vitro culture of stem cells may cause a change in the biochemistry of the cells and may result in stem cells which do not behave as they might be expected to in vivo. Accordingly, there is disagreement in the scientific community as to whether some presently maintained cell lines are truly to be considered stem cells.

The earliest type of stem cell, embryonic stem cells (ESCs), originate in the blastocyst stage of an embryo, which in the human would be about four or five days old and contain up to about 150 cells. ESCs can differentiate into any cell type in the adult body, of which there are over two hundred types. Obviously, such differentiation would require the proper nutrition and growth conditions, as well as the correct stimuli for development.

To date, just about all research has been based on mouse embryonic stem cells (mESCs) and on human embryonic stem cells (hESCs). These two cells types have the required characteristics of stem cells but demand quite different culture conditions and environment, without which they will quickly differentiate, losing their stem cell potential. Human ESCs are further defined by the presence of certain cell markers, including transcription factors and cell surface proteins. These include Oct-4, NANOG, and Sox2, all transcription factors which help suppress genes that, if active, would lead to differentiation. Also, SSEA3 and SSEA4 cell surface glycolipids as well as Tra-1-60 and Tra-1-81 surface antigens. Other markers which may help identify a stem cell are being studied as well.

An "adult stem cell" is one which is found in the fully developed organism but which yet retains its ability to divide to form others like itself and also retains the ability to differentiate into more specialized cells. These cells are also known as somatic stem cells and are found not only in adults but also in children. Somatic stem cells are typically restricted in their differential capacity so that they are able to form a limited range of more specialized cells. Accordingly, they are often named by their tissue of origin, for example, mesenchymal stem cells, endothelial stem cells, and others.

Much research has been devoted to environmental factors that influence the differentiation of stem cells or even the regression of differentiated cells back to undifferentiated stem cells. In fact, there have been very recently two reports describing the generation of stem cells from fully differentiated skin cells. The potential is there for regressing fully differentiated cells into stem cells which can then be differentiated into yet other types of specialized cells. This is of great interest, as it would completely render moot the argument over destruction of a human embryo in order to obtain hESCs.

When stem cells divide, they may form two stem cell daughter cells (symmetric division), or may form one stem cell and one daughter cell having less potential (asymmetric division). How this process is determined is unknown at this time. One school of thought holds that the specific segregation of cell membrane proteins may determine asymmetric division. In our view, this uneven segregation of cell membrane proteins is more likely a symptom of asymmetric division, rather than a cause of it. Another school of thought holds that environmental factors influence stem cells to remain undifferentiated. If these environmental factors change in some way, then the stem cells will differentiate.

SUMMARY OF THE INVENTION

With the foregoing in mind, the present invention advantageously provides methods of maintaining the pluripotency of cultured human bone marrow mesenchymal stem cells by providing environmental factors that influence their state.

A method of the invention provides for up-regulating genes that maintain the pluripotency and proliferation of cultured human bone marrow mesenchymal stem cells by culturing the stem cells in a nutrient medium together with cells from a limb of a limb-regenerating animal. The inventors theorize, while not wishing to be bound by this particular explanation of the invention, that limb cells from a limb-regenerating animal possess factors which, when present in the culture medium, will influence human bone marrow mesenchymal stem cells to proliferate and to maintain their pluripotency. These pluripotency maintenance factors (PMF) may be polynucleotides, polypeptides, or others. Nevertheless, when in co-culture with limb-regenerating cells, the human stem cells demonstrate up-regulation of several genes involved in pluripotency and proliferation. In the method, the limb-regenerating animal is preferably a species of the family Polychrotidae and, particularly, the typical garden lizard species found in Florida. It should be understood that PMF may be provided in the stem cell culture medium whether or not the PMF-producing cells themselves are in co-culture with the stem cells.

The invention additionally provides a method of up-regulating genes maintaining pluripotency and proliferation in cultured human bone marrow mesenchymal stem cells, the method comprising culturing the stem cells in a nutrient medium together with mouse embryonic stem cells. As above, the proposed mechanism of action involves the mouse embryonic stem cells producing various cellular factors which are then present in the culture medium and which influence the metabolism of the human stem cells by up-regulating a number of genes. As noted above, the PMF may be provided in a cell-free culture medium for stem cells.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which:

FIG. 1 comprises FIGS. 1A, 1B and 1C and shows in 1A control human mesenchymal stem cells (hMSCs), in 1B and 1C views of hMSCs co-cultured with lizard tail extract according to an embodiment of the present invention.

DETAILED DESCRIPTION OF THE PREFERRED EMBODIMENT

Figure 2:
FIG. 2 is a fluorescence microscopy view of hMSCs treated with mito-red and co-cultured with mESC-YFP for 48 hours; immunostaining where red portions are human nucleoli and green portions are NANOG.

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, or other references mentioned herein are incorporated by reference in their entirety. In case of conflict, the present specification, including any definitions, will control. In addition, the materials, methods and examples given are illustrative in nature only and not intended to be limiting. Accordingly, this invention may be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

Modifying Stem Cell Characteristics Using Cell Extracts

Cellular dedifferentiation aims to modify the developmental potential of a cell. Our previous research has demonstrated the ability to modify the developmental potential of a cell by treatment with nucleotide derivatives or chromatin modifying compounds. Following treatment of human bone marrow mesenchymal stem cells with these drugs, there was an up-regulation of stem cell markers. Additionally, we have also demonstrated that forced expression of stem cell genes up-regulated the expression of other genes responsible in self-renewal and pluripotency. We demonstrated that when these genes are up-regulated, cells are able to develop beyond their normal cell fates. For example, human mesenchymal stem cells can develop into neurons (including dopaminergic neurons), glial, inner ear hair cells, etc.

The present disclosure demonstrates an additional method for modifying the developmental potential of cells using extracts of other cells. Specifically, we have shown that culturing stem cells in a nutrient medium containing cell products from a lower species, the tail of an animal capable of limb regeneration (for example, the common garden lizards found in Florida, commonly known as Anoles and, in general, the family Polychrotidae) up-regulates genes associated with pluripotency (such as Oct4 and Sox2) as well as increasing proliferation (TERT, and TERF). Genes highlighted in green show up-regulation of stem cell genes relative to controls using real-time PCR. Morphological analysis of cells in culture reveals phenotypic alterations comparable to more primitive (embryonic-like) stem cells rather than the cells' more typical spindle-shaped morphology. Table 1 summarizes the results of co-culturing mesenchymal stem cells with lizard tail sections and shows up-regulation of at least three genes associated with maintaining the potency of the stem cells: Oct4, Sox2, TERT and TERF. FIG. 1 illustrates aspects of Table 1.

We then also examined if exposure to less differentiated cells, for example, mouse embryonic stem cells, could alter the cell fate of the host cells. Culturing human mesenchymal stem cells in direct contact with cells of another lower species, specifically, mouse embryonic stem cells, reveals dramatic up-regulation of stem cell genes (highlighted in green) as well as morphological changes. Fluorescent microscopy reveals that mitochondrial-labeled human mesenchymal stem cells show expression of NANOG following co-culture. Taken together, we believe these data demonstrate that cellular extracts can act on a human cell and modify and/or expand its developmental potential through the up-regulation of stem cell genes. Table 2 summarizes the results of co-culturing mesenchymal stem cells with mouse embryonic stem cells and shows up-regulation of multiple genes associated with maintaining the potency of the stem cells: Lefty, Oct4, DNMT3L, Zfp, HRPT, Activin RIIa, Sox2, FoxD3, NANOG, TERT, TERF and Eras. FIG. 2 illustrates aspects of Table 2.

An extract from the embryonic stem cells or regenerative limb would be protein extracts. Protein extracts can be collected through ultra-centrifugation or other protein purification techniques. The co-culture with mouse embryonic stem cells was employed to assure that changes demonstrated in the human bone marrow mesenchymal stem cell culture were truly changes in the human stem cells (this was checked using human specific primers) rather than contamination from the mouse stem cell cultures.

Potential applications of the present invention include new cell culture media formulations containing cell products that induce modifications in stem cells. Also, the invention shows the potential use of cell product extracts to improve regeneration and cellular repair, improving stem cell transplants (including those derived from nuclear transfer) by treating cells with concentrated extracts or placing the extracts within a cell cytoplasm.

Accordingly, in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

culturing the human bone marrow mesenchymal stem cells in a nutrient medium together with cells from a tail of a tail-regenerating lizard;

wherein the up-regulated genes comprise genes responsible for maintaining pluripotency of the stem cells or genes responsible for cell proliferation; or both;

wherein the genes responsible for maintaining pluripotency of the stem cells are selected from the group consisting of Oct4, Sox2, and combinations thereof; and wherein the genes responsible for cell proliferation are selected from the group consisting of TERT, TERF, and combinations thereof.

TABLE 1

Co-culture with tail sections shows up-regulation of embryonic stem cell markers in human bone marrow stem cells.
61120 cDNA Control MSC Tail co-culture, mESC-YFP co-culture, 2m Nanog transfection
MSC Tail co-culture

|  | Control | Tail co-culture | CtCont-CtHath1 | Pfaffl eq | CtCon-CtTail-hMSC co-culture | Beta Actin | Ratio of target genes |
|---|---|---|---|---|---|---|---|
| GAPDH | 40 | 19.77 | 20.23 | 1229807 | 5.43 | 43.11147 | 28526.2 |
| Lefty | 30.56 | 25.82 | 4.74 | 26.72281 | 5.43 | 43.11147 | 0.619854 |
| Connexin | 28.35 | 26.95 | 1.4 | 2.639016 | 5.43 | 43.11147 | 0.061214 |
| Oct4 | 33.82 | 25.15 | 8.67 | 407.3147 | 5.43 | 43.11147 | 9.447941 |
| DPPA5 | 40 | 36.82 | 3.18 | 9.063071 | 5.43 | 43.11147 | 0.210224 |
| DNMT3L | 40 | 37.58 | 2.42 | 5.35171 | 5.43 | 43.11147 | 0.124137 |
| Zfp | 34.61 | 34.38 | 0.23 | 1.172835 | 5.43 | 43.11147 | 0.027205 |
| HPRT1 | 40 | 40 | 0 | 1 | 5.43 | 43.11147 | 0.023196 |
| bActin | 24.11 | 18.68 | 5.43 | 43.11147 | 5.43 | 43.11147 | 1 |
| BMPR1a | 30.49 | 29.91 | 0.58 | 1.494849 | 5.43 | 43.11147 | 0.034674 |
| Activin RIIa | 30.01 | 32.57 | −2.56 | 0.169576 | 5.43 | 43.11147 | 0.003933 |
| Sox2 | 40 | 29.03 | 10.97 | 2005.853 | 5.43 | 43.11147 | 46.52712 |
| FoxD3 | 36.96 | 40 | −3.04 | 0.121582 | 5.43 | 43.11147 | 0.0282 |
| Nanog | 23.89 | 23.88 | 0.01 | 1.006956 | 5.43 | 43.11147 | 0.023357 |
| TERT | 37.78 | 28.63 | 9.15 | 568.0996 | 5.43 | 43.11147 | 13.17746 |
| TERF | 40 | 27.69 | 12.31 | 5077.843 | 5.43 | 43.11147 | 117.784 |
| Eras | 28.94 | 27.02 | 1.92 | 3.784231 | 5.43 | 43.11147 | 0.087778 |

TABLE 2

Co-culture with mouse embryonic stem cells shows up-regulation of embryonic stem cell markers in human bone marrow stem cells.
61204 hMSC mESC-YFP direct co-culture 1w and controls p3 MSC

|  | Control | mESC co-culture | CtCont-CtHath1 | Pfaffl eq. | CtCon-CthMSC co-culture | Beta Actin | Ratio of target genes |
|---|---|---|---|---|---|---|---|
| Lefty | 32.41 | 32.15 | 0.26 | 1.197479 | −5.74 | 0.018711 | 64 |
| Connexin | 22.88 | 42.95 | −20.07 | 9.09E−07 | −5.74 | 0.018711 | 4.86E−05 |
| Oct4 | 29.53 | 31.34 | −1.81 | 0.285191 | −5.74 | 0.018711 | 15.24221 |
| DPPA5 | 35.43 | 41.59 | −6.16 | 0.013985 | −5.74 | 0.018711 | 0.747425 |
| DNMT3L | 37.76 | 36.94 | 0.82 | 1.765406 | −5.74 | 0.018711 | 94.35323 |
| Zfp | 32.95 | 35.9 | −2.95 | 0.129408 | −5.74 | 0.018711 | 6.916298 |
| HRPT | 26.75 | 29.51 | −2.76 | 0.147624 | −5.74 | 0.018711 | 7.889862 |
| bActin | 18.68 | 24.42 | −5.74 | 0.018711 | −5.74 | 0.018711 | 1 |
| BMPR1a | 25.41 | 39.72 | −14.31 | 4.92E−05 | −5.74 | 0.018711 | 0.002631 |
| Activin RIIa | 34.61 | 35.47 | −0.86 | 0.550953 | −5.74 | 0.018711 | 29.446 |
| Sox2 | 37.88 | 25.88 | 12 | 4096 | −5.74 | 0.018711 | 218913.3 |
| FoxD3 | 32.31 | 32.64 | −0.33 | 0.795536 | −5.74 | 0.018711 | 42.51795 |
| Nanog | 28.79 | 30.84 | −2.05 | 0.241484 | −5.74 | 0.018711 | 12.90627 |
| TERT | 35.37 | 28.65 | 6.72 | 105.4197 | −5.74 | 0.018711 | 5634.219 |
| TERF | 26.31 | 29.98 | −3.67 | 0.078563 | −5.74 | 0.018711 | 4.198867 |
| Eras | 18.22 | 30.84 | −2.62 | 0.162668 | −5.74 | 0.018711 | 8.693879 |

That which is claimed:

1. A method of up-regulating one or more genes in cultured human bone marrow mesenchymal stem cells, the method comprising:

2. The method of claim 1, wherein the tail-regenerating lizard is a species of the family Polychrotidae.

3. The method of claim 1, wherein the human bone marrow mesenchymal stem cells are cultured human bone marrow mesenchymal stem cells.

4. A method of up-regulating one or more genes in human bone marrow mesenchymal stem cells, the method comprising:
co-culturing human bone marrow mesenchymal stem cells with a nutrient medium comprising cells from a tail section of an Anoles lizard; wherein the up-regulated genes comprise a member from the group selected from Oct4, Sox2, TERT, TERF, and combinations thereof.

* * * * *